United States Patent [19]

Ogawa et al.

[11] Patent Number: 4,740,601

[45] Date of Patent: Apr. 26, 1988

[54] IMIDAZOLE DERIVATIVES HAVING ANTIMICROBIAL ACTIVITIES

[75] Inventors: Masaki Ogawa, Narashino; Hideaki Matsuda, Abiko; Takemitsu Asaoka; Junji Oono, both of Narita; Tatsuhiko Katori, Tone, all of Japan

[73] Assignee: SS Pharmaceutical Co., Ltd., Tokyo, Japan

[21] Appl. No.: 941,318

[22] Filed: Dec. 15, 1986

[30] Foreign Application Priority Data

Dec. 23, 1985 [JP] Japan .................................. 60-289798
Jul. 9, 1986 [JP] Japan .................................. 61-161524

[51] Int. Cl.$^4$ .................. C07D 405/06; C07D 233/04; C07D 233/54; A61K 31/415
[52] U.S. Cl. ...................................... 548/336; 548/511
[58] Field of Search .............................. 548/336, 341

[56] References Cited

FOREIGN PATENT DOCUMENTS 62-149666 7/1987 Japan .................................. 548/336

OTHER PUBLICATIONS

Chemical Abstracts, vol. 93, Abstract No. 71640q, 1980, p. 967.
Chemical Abstracts, vol. 97, Abstract No. 72366z, 1982, p. 636.

Primary Examiner—Henry R. Jiles
Assistant Examiner—Zinna Northington
Attorney, Agent, or Firm—Oblon, Fisher, Spivak, McClelland & Maier

[57] ABSTRACT

An imidazole derivative having antimicrobial activities against bacteria, fungi, yeast, pathogenic plant fungi and the like represented by the following general formula (I):

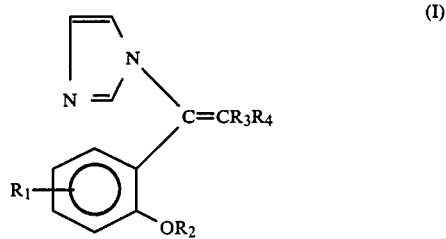

wherein $R_1$ means a hydrogen or halogen atom or a lower alkyl group, $R_2$ denotes a hydrogen atom or an alkyl, alkenyl, haloalkyl or substituted or unsubstituted benzyl group, $R_3$ stands for a hydrogen or halogen atom, and $R_4$ is a substituted or unsubstituted benzylthio group, a phenylthio, alkylthio, alkenylthio, furfurylthio, alkoxy or phenoxy group or a halogen atom; or an acid addition salt thereof.

1 Claim, No Drawings

IMIDAZOLE DERIVATIVES HAVING ANTIMICROBIAL ACTIVITIES

BACKGROUND OF THE INVENTION

1. Field of the Invention

This invention relates to novel imidazole derivatives and their acid addition salts, and more specifically to imidazole derivatives and their acid addition salts which have antimicrobial activities against bacteria, fungi, yeasts, pathogenic plant fungi and the like and are hence usable as medicines, agricultural chemicals, antiseptics and so on.

2. Discussion of the Background

There have already been known a variety of imidazole derivatives having antimicrobial activities against fungi and the like, but their effects are still insufficient. There is thus a strong demand for the development of compounds having still better antibacterial activities.

SUMMARY OF THE INVENTION

Accordingly, an object of the present invention is to provide imidazole derivatives having antibacterial activities better than conventionally-known imidazole derivatives.

The present inventors have synthesized various imidazole derivatives and investigated their antibacterial activities. As a result, it has been found that imidazole derivatives represented by the following general formula (I) have excellent antimicrobial activities against bacteria, fungi, yeasts, pathogenic plant fungi and the like, leading to completion of this invention.

Namely, the present invention provides an imidazole derivative represented by the following general formula (I):

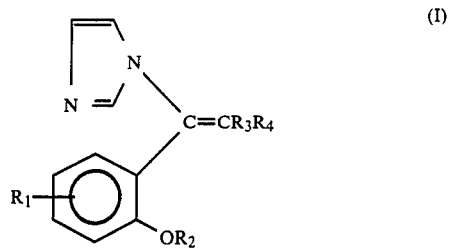

wherein $R_1$ means a hydrogen or halogen atom or a lower alkyl group, $R_2$ denotes a hydrogen atom or an alkyl, alkenyl, haloalkyl or substituted or unsubstituted benzyl group, $R_3$ stands for a hydrogen or halogen atom, and $R_4$ is a substituted or unsubstituted benzylthio group, a phenylthio, alkylthio, alkenylthio, furfurylthio, alkoxy or phenoxy group or a halogen atom; or an acid addition salt thereof.

The compounds (I) of this invention, which are obtained in the below-described manner, have excellent antimicrobial activities against bacteria, fungi, yeasts, pathogenic plant fungi and the like and are hence useful as medicines, agricultural chemicals, antiseptics and so on.

A more complete appreciation of the invention and many of the attendant advantages thereof will be readily obtained as the same becomes better understood by reference to the following detailed description.

DETAILED DESCRIPTION OF THE PREFERRED EMBODIMENTS

The compound (I) of this invention may be prepared, for example, in accordance with the following reaction scheme, namely, by reacting a phenol derivative (II) with an N,N'-thionyldiimidazole (III) or reacting the phenol derivative (II) with 1-imidazolylsulfinyl chloride (IV) in the presence of a base, e.g., triethylamine to obtain an imidazole derivative (Ia), and if desired, reacting the imidazole derivative (Ia) further with an alkylating, alkenylating, haloalkylating or substituted or unsubstituted benzylating agent (V) to form another imidazole derivative (Ib).

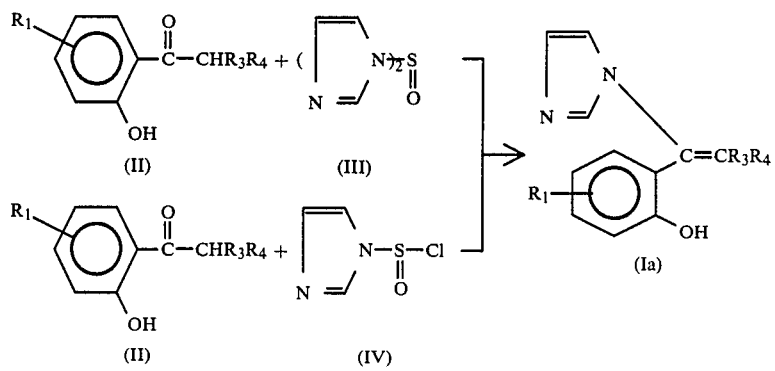

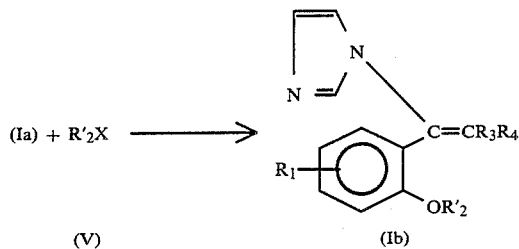

wherein $R_1$, $R_2$, $R_3$ and $R_4$ have the same meaning as defined above $R_2'$ denotes an alkyl, alkenyl, haloalkyl or substituted or unsubstituted benzyl group, and X means a halogen atom, benzenesulfonyloxy group, p-toluenesulfonyloxy group, methanesulfonyloxy group, trichloromethanesulfonyloxy group or the like.

Phenol compounds (II), which are starting materials in the present invention, are either known compounds or those readily available in accordance with known processes. For example, they can each be prepared by any one of the following processes.

(1) In formula (II), $R_4$: a substituted or unsubstituted benzylthio group or a phenylthio, alkylthio, alkenylthio or furfurylthio group [Compound (IIa)]:

A 2'-hydroxy-2-haloacetophenone or its derivative (VI) and a thiol compound (VII) are reacted in the presence of an alkali.

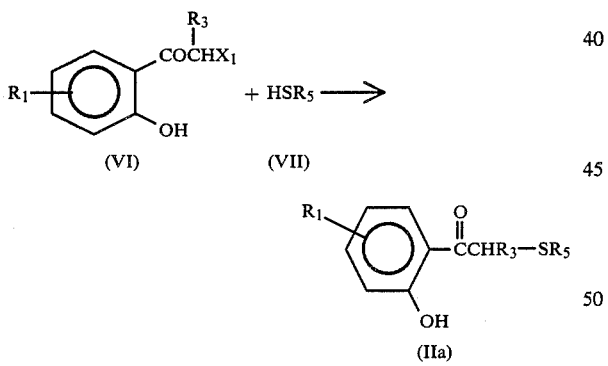

wherein $R_1$ and $R_3$ have the same meaning as defined above, and $R_5$ denotes a substituted or unsubstituted benzyl group or a phenyl, alkyl, alkenyl or furfuryl group, and $X_1$ stands for a halogen atom.

As thiol compounds (VII), may be used thiophenol, benzyl mercaptan which may contain one or more substituent groups, alkyl mercaptans, alkenyl mercaptans and furfuryl mercaptan.

(2) In formula (II), $R_4$: an alkoxy or phenoxy group [Compound (IIb)]:

An alkoxyacetonitrile or its derivative (VIII) is reacted with 2-benzyloxyphenylmagnesium bromide or its derivative (IX) to obtain an acetophenone derivative (X), followed by its catalytic reduction to conduct debenzylation.

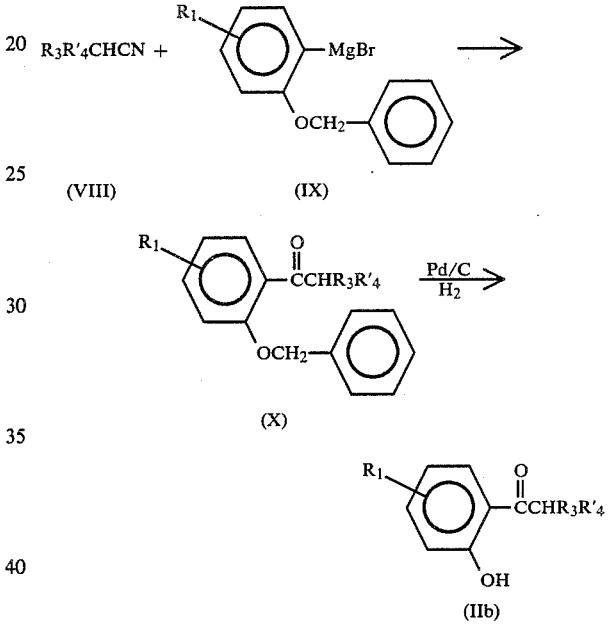

wherein $R_1$ and $R_3$ have the same meaning as defined above and $R_4'$ denotes an alkoxy or phenoxy group. (3) In formula (II), $R_4$: a halogen atom [Compound (IIc)]:

An ethyl monohaloacetate (XI) is reacted with 2-benzyloxyphenylmagnesium bromide (IX) at a low temperature (below $-40°$ C.) and the resulting acetophenone derivative (XII) is subjected to debenzylation with boron trichloride, thereby preparing the compound (IIc).

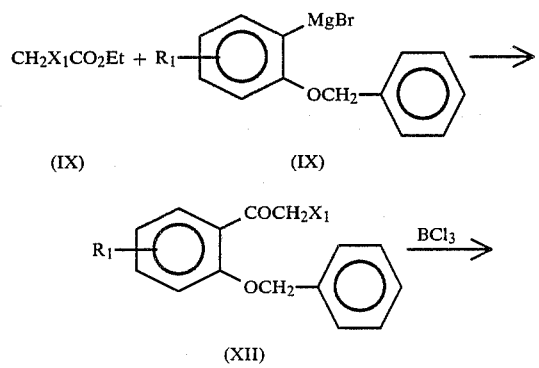

-continued

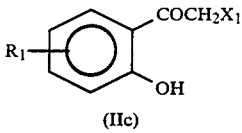

(IIc)

where $R_1$ and $X_1$ have the same meaning as defined above.

The reaction between the compound (II) and the compound (III) or (IV) is effected by reacting them in a suitable solvent such as methylene chloride, chloroform, dimethylsulfoxide, acetonitrile, dimethylformamide or the like, at room temperature or with ice-cooling or heating, for 15 minutes-several hours. As exemplary bases useful in the reaction between the compound (II) and the compound (IV), may be mentioned, besides triethylamine referred to above, tertiary amines such as trimethylamine, tri-n-propylamine, N-methylmorpholine and N-ethylmorpholine.

On the other hand, the reaction between the compound (Ia) and the alkylating, alkenylating, haloalkylating or substituted or unsubstituted benzylating agent represented by the formula (V) is effected by reacting them in the presence of an alkali or by reacting an alkali salt of the compound (Ia) with the compound (V). As illustrative examples of the alkali employed in this reaction, may be mentioned sodium hydroxide, potassium hydroxide, sodium hydride, sodium alcoholate and the like. Illustrative examples of the alkali salt may include the sodium salt, potassium salt and so on. As a reaction solvent, may for example be mentioned dimethylformamide, benzene, methanol, ethanol, tetrahydrofuran, ether or the like. The reacton is conducted at room temperature or with heating for several ten minutes-several ten hours. Except for the case where $R_3$ and and $R_4$ are the same, the thus-obtained compound (I) of this invention contains two types of isomers A and B. Each of these isomers has antibacterial activities, and they may hence be used either singly or as a mixture.

When it is desired to obtain either one of the isomers of the compound (I) of this invention, it is only necessary to isolate the respective isomers by a known separation method such as column chromatography or to prepare selectively the desired isomer only by adjusting the reaction conditions.

The compound (I) of this invention can be converted into its acid addition salt by a method known per se in the art. As exemplary acid addition salts, may be mentined those of acids acceptable from the standpoint of pharmacology and pharmaceutical technology, for example, inorganic acids such as hydrochloric acid, sulfuric acid, nitric acid and hydrobromic acid as well as organic acids such as acetic acid, oxalic acid, fumaric acid, maleic acid, citric acid, malic acid and succinic acid.

Antibacterial activities of certain representative compounds of this invention, which had been obtained in the above-described manner, were investigated. Results are summarized in Table 1, in which the compound numbers correspond to those to be given in Examples which will be described herein.

TABLE 1-A

| Microorganism tested | Compound tested MIC (μg/ml) | | | |
|---|---|---|---|---|
| | Compound 3 | Compound 4 | Compound 7 | Compound 8 |
| Bacillus subtilis ATCC 6633 | 1.56 | 6.25 | 25 | 3.12 |
| Staphylococcus aureus FDA 209P | 12.5 | 25 | 50 | 25 |
| Staphylococcus aureus Terajima | 6.25 | 12.5 | 25 | 6.25 |
| Staphylococcus aureus Smith | 6.25 | 12.5 | 12.5 | 6.25 |
| Staphylococcus epidermidis ATCC 12228 | 3.12 | 12.5 | 25 | 6.25 |
| Sarcina lutea ATCC 9341 | 1.56 | 6.25 | 12.5 | 3.12 |
| Streptococcus faecalis IFO 12964 | 6.25 | 12.5 | 50 | >100 |
| Micrococcus lysodeixticus IFO 3333 | 0.78 | 3.12 | 6.25 | 1.56 |
| Candida albicans NHL 4019 | 50 | 25 | 100 | >100 |
| Candida albicans Yu-1200 | >100 | >100 | >100 | >100 |
| Saccharomyces cerevisiae ATCC 9763 | <0.2 | <0.2 | <0.2 | <0.2 |
| Saccharomyces ruxii 6507 | <0.2 | <0.2 | 0.78 | <0.2 |
| Aspergillus niger ATCC 9642 | 0.39 | 1.56 | 12.5 | 12.5 |
| Penicillium chrysogenum ATCC 6010 | 50 | 3.12 | 50 | 12.5 |
| Trichophyton mentagrophytes QM 248 | <0.2 | <0.2 | 3.12 | 0.39 |
| Trichophyton mentagrophytes IFO 5812 | <0.2 | <0.2 | 0.78 | 0.39 |
| Trichophyton tonsurans IFO 5928 | <0.2 | <0.2 | <0.2 | <0.2 |
| Trichophyton rubrum NHL J | <0.2 | <0.2 | <0.2 | <0.2 |
| Microsporum gypseum IFO 8231 | <0.2 | <0.2 | 1.56 | 0.39 |
| Microsporum audounii IFO 6074 | <0.2 | <0.2 | <0.2 | <0.2 |
| Microsporum cookei IFO 8303 | 6.25 | 1.56 | 12.5 | 12.5 |
| Epidermophyton floccosum IFO 9045 | 3.12 | 1.78 | 6.25 | 6.25 |
| Aspergillus oryzae IMF 4014 | 6.25 | 1.56 | 6.25 | 12.5 |
| Cladosporium fulvum IAM 5006 | 12.5 | 25 | 100 | >100 |
| Fusarium moniliforme IAM 5062 | >100 | 0.78 | 6.25 | 12.5 |
| Helminthosporium sesamum IAM 5012 | <0.2 | <0.2 | 0.39 | 0.78 |
| Pyricularia oryzae IAM 5016 | <0.2 | <0.2 | <0.2 | <0.2 |
| Debaryomyces kloeckeri IFO 0015 | 6.25 | 6.25 | 25 | 6.25 |
| Gibberella fujikuroi IAM 8046 | 25 | 0.78 | 6.25 | 6.25 |

TABLE 1-B

| Microorganism tested | Compound tested MIC (μg/ml) | | | | |
|---|---|---|---|---|---|
| | Comp. 27 | Comp. 34 | Comp. 39 | Comp. 46 | Comp. 49 |
| Bacillus subtilis ATCC 6633 | 6.25 | 3.12 | 12.5 | 6.25 | 3.12 |
| Staphylococcus aureus FDA 209P | 12.5 | 12.5 | 25 | 12.5 | 12.5 |
| Staphylococcus aureus Terajima | 6.25 | 12.5 | 25 | 12.5 | 6.25 |

TABLE 1-B-continued

| Microorganism tested | Compound tested MIC (μg/ml) | | | | |
|---|---|---|---|---|---|
| | Comp. 27 | Comp. 34 | Comp. 39 | Comp. 46 | Comp. 49 |
| *Staphylococcus aureus* Smith | 12.5 | 12.5 | 25 | 12.5 | 12.5 |
| *Staphylococcus epidermidis* ATCC 12228 | 6.25 | 3.12 | 25 | 6.25 | 3.12 |
| *Sarcina lutea* ATCC 9341 | 3.12 | 1.56 | 12.5 | 6.25 | 3.12 |
| *Streptococcus faecalis* IFO 12964 | 12.5 | 12.5 | 25 | 12.5 | 6.25 |
| *Micrococcus lysodeixticus* IFO 3333 | 1.56 | 0.39 | 6.25 | 3.12 | 1.56 |
| *Candida albicans* NHL 4019 | 25 | 50 | 25 | 25 | 25 |
| *Candida albicans* Yu-1200 | 50 | 50 | 50 | 50 | 25 |
| *Saccharomyces cerevisiae* ATCC 9763 | <0.2 | <0.2 | 0.39 | <0.2 | 50 |
| *Saccharomyces ruxii* 6507 | <0.2 | <0.2 | 0.78 | 0.78 | <0.2 |
| *Aspergillus niger* ATCC 9642 | 0.39 | 0.78 | 1.56 | 1.56 | <0.2 |
| *Penicillium chrysogenum* ATCC 6010 | 1.56 | 3.12 | 1.56 | 1.56 | 6.25 |
| *Trichophyton mentagrophytes* QM 248 | <0.2 | <0.2 | 0.39 | <0.2 | <0.2 |
| *Trichophyton mentagrophytes* IFO 5812 | <0.2 | <0.2 | 0.39 | <0.2 | <0.2 |
| *Trichophyton tonsurans* IFO 5928 | <0.2 | <0.2 | 0.39 | <0.2 | <0.2 |
| *Trichophyton rubrum* NHL J | <0.2 | <0.2 | <0.2 | <0.2 | <0.2 |
| *Microsporum gypseum* IFO 8231 | <0.2 | <0.2 | 0.39 | <0.2 | <0.2 |
| *Microsporum audounii* IFO 6074 | <0.2 | <0.2 | <0.2 | <0.2 | <0.2 |
| *Microsporum cookei* IFO 8303 | <0.2 | 1.56 | 1.56 | 1.56 | 1.56 |
| *Epidermophyton floccosum* IFO 9045 | <0.2 | 1.56 | 1.56 | 1.56 | 0.78 |
| *Aspergillus oryzae* IMF 4014 | <0.2 | 1.56 | 0.78 | 0.78 | 0.78 |
| *Cladosporium fulvum* IAM 5006 | 3.12 | 25 | 25 | 12.5 | 25 |
| *Fusarium moniliforme* IAM 5062 | <0.2 | 0.39 | 0.78 | 1.56 | 1.56 |
| *Helminthosporium sesamum* IAM 5012 | <0.2 | <0.2 | 0.39 | 1.56 | 0.39 |
| *Pyricularia oryzae* IAM 5016 | <0.2 | <0.2 | <0.2 | <0.2 | <0.2 |
| *Debaryomyces kloeckeri* IFO 0015 | 1.56 | 0.78 | 6.25 | 12.5 | 12.5 |
| *Gibberella fujikuroi* IAM 8046 | <0.2 | <0.2 | 0.78 | 0.39 | 0.39 |

TABLE 1-C

| Microorganism tested | Compound tested MIC (μg/ml) | | | | |
|---|---|---|---|---|---|
| | Comp. 64 | Comp. 65 | Comp. 73 | Comp. 83 | Comp. 93 |
| *Bacillus subtilis* ATCC 6633 | 6.25 | 3.12 | 6.25 | 6.25 | 12.5 |
| *Staphylococcus aureus* FDA 209P | 25 | 12.5 | 12.5 | 12.5 | 25 |
| *Staphylococcus aureus* Terajima | 6.25 | 6.25 | 6.25 | 6.25 | 25 |
| *Staphylococcus aureus* Smith | 12.5 | 6.25 | 12.5 | 12.5 | 25 |
| *Staphylococcus epidermidis* ATCC 12228 | 6.25 | 6.25 | 6.25 | 6.25 | 25 |
| *Sarcina lutea* ATCC 9341 | 6.25 | 3.12 | 6.25 | 3.12 | 25 |
| *Streptococcus faecalis* IFO 12964 | 25 | 12.5 | 12.5 | 12.5 | 50 |
| *Micrococcus lysodeixticus* IFO 3333 | 1.56 | 1.56 | 3.12 | 1.56 | 6.25 |
| *Candida albicans* NHL 4019 | >100 | >100 | 50 | 50 | 100 |
| *Candida albicans* Yu-1200 | >100 | >100 | 50 | 12.5 | >100 |
| *Saccharomyces cerevisiae* ATCC 9763 | 50 | 25 | 50 | 25 | <0.2 |
| *Saccharomyces ruxii* 6507 | 1.56 | 6.25 | 1.56 | <0.2 | <0.2 |
| *Aspergillus niger* ATCC 9642 | 12.5 | >100 | 12.5 | 12.5 | >100 |
| *Penicillium chrysogenum* ATCC 6010 | 12.5 | >100 | 6.25 | 25 | >100 |
| *Trichophyton mentagrophytes* QM 248 | 0.78 | 12.5 | 3.12 | <0.2 | 1.56 |
| *Trichophyton mentagrophytes* IFO 5812 | <0.2 | 3.12 | 1.56 | <0.2 | <0.2 |
| *Trichophyton tonsurans* IFO 5928 | 3.12 | 12.5 | 3.12 | <0.2 | 1.56 |
| *Trichophyton rubrum* NHL J | <0.2 | 3.12 | 1.56 | <0.2 | 0.39 |
| *Microsporum gypseum* IFO 8231 | 6.25 | 12.5 | 3.12 | 1.56 | 6.25 |
| *Microsporum audounii* IFO 6074 | <0.2 | 6.25 | 0.78 | <0.2 | <0.2 |
| *Microsporum cookei* IFO 8303 | 12.5 | 100 | 6.25 | 6.25 | 12.5 |
| *Epidermophyton floccosum* IFO 9045 | 6.25 | 100 | 6.25 | 6.25 | 25 |
| *Aspergillus oryzae* IMF 4014 | 6.25 | >100 | 6.25 | 12.5 | >100 |
| *Cladosporium fulvum* IAM 5006 | >100 | >100 | 6.25 | 12.5 | >100 |
| *Fusarium moniliforme* IAM 5062 | 50 | >100 | 12.5 | 25 | >100 |
| *Helminthosporium sesamum* IAM 5012 | 6.25 | 100 | 6.25 | 6.25 | 50 |
| *Pyricularia oryzae* IAM 5016 | <0.2 | 1.56 | 1.56 | <0.2 | 0.39 |
| *Debaryomyces kloeckeri* IFO 0015 | >100 | >100 | 3.12 | 6.25 | 6.25 |
| *Gibberella fujikuroi* IAM 8046 | 25 | >100 | 6.25 | 25 | >100 |

Having generally described this invention, a further understanding can be obtained by reference to certain specific examples which are provided herein for purpose of illustration only and are not intended to be limiting unless otherwise specified.

EXAMPLE 1

To a suspension of 4.08 g of imidazole and 30 ml of dry methylene chloride, 1.78 g of thionyl chloride was added with ice-cooling. After stirring the reaction mixture for 30 minutes, 2.58 g of 2-benzylthio-2'-hydroxyacetophenone was added, followed by further stirring at room temperature for 2 hours. Ice water was added to the reaction mixture, followed by extraction with methylene chloride. The organic, i.e., methylene chloride layer was washed with water, dried over magnesium sulfate and then concentrated. The residue was dissolved in chloroform and was then subjected to chromatography on a silica gel column. Upon concentration of the resultant eluate, there were obtained 180 mg of Isomer A (m.p. 196°–198° C.; Compound 1) and 1.0 g of Isomer B (m.p. 136.5°–138° C.; Compound 2) of 1-(2-hydroxyphenyl)-1-imidazolyl-2-benzylthioethylene (in formula (I), $R_1$, $R_2$, $R_3$=H, $R_4$=—SCH$_2$C$_6$H$_5$), both, as colorless crystals.

EXAMPLE 2

Dissolved in 2 ml of dry dimethylformamide was 100 mg of Compound 1 obtained above, to which 15 mg of 60% sodium hydride was added, followed by stirring at room temperature. Thirty minutes later, 45 mg of n-propyl bromide was added. The resultant mixture was left over at room temperature for 4 hours. The reaction mixture was then added with water, followed by its extraction with ethyl ether. The ether extract was dried over magnesium sulfate and the ether was then distilled off. The residue was purified by chromatography on a silica gel column. From the resulting chloroform eluate, 90 mg of Isomer A (Compound 3) of 1-(2-n-propyloxyphenyl)-1-imidazolyl-2-benzylthioethylene (in formula (I), $R_1$, $R_3$=H, $R_2$=n—C$_3$H$_7$, $R_4$=—SCH$_2$C$_6$H$_5$) was obtained as colorless crystals.

EXAMPLE 3

Two hundred milligrams of Compound 3 obtained in Example 2 were used. After an addition of hydrogen chloride in an equivalent amount, the resultant precipitate was recrystallized from ethyl acetate/acetone to obtain 120 mg of Isomer A (Compound 17) of 1-(2-n-propyloxyphenyl)-1-imidazolyl-2-benzylthioethylene hydrochloride as colorless crystals.

EXAMPLE 4

Using the compound (or its isomers) obtained in Example 1, the compounds given in Table 2-A were obtained in the same manner as in Example 2. The compounds obtained in Examples 1–3 are also shown in the table.

TABLE 2-A

| Comp. No. | Structure Formula (I) | | | | Isomer type | Characteristics Appearance (m.p. °C.) | NMR δ ppm in CDCl$_3$ | IR $\nu_{max}^{NaCl}$cm$^{-1}$ |
|---|---|---|---|---|---|---|---|---|
| | $R_1$ | $R_2$ | $R_3$ | $R_4$ | | | | |
| 1 | H | H | H | —SCH$_2$C$_6$H$_5$ | A | Colorless crystal (196-198) | 3.98(2H,s) 6.64(1H,s) 6.70-7.40 (11H,m) 7.64(1H,br) | *1600,1495,1445, 1080 |
| 2 | H | H | H | —SCH$_2$C$_6$H$_5$ | B | Colorless crystal (136.5-138) | 3.90(2H,s) 6.36(1H,s) 6.70-7.60 (12H,m) | *1600,1495,1450, 1225 |
| 3 | H | n-C$_3$H$_7$ | H | —SCH$_2$C$_6$H$_5$ | A | Colorless crystal (82.5-84.0) | 0.88(3H,t) 1.52(2H,m) 3.78(2H,t) 3.94(2H,s) 6.70(1H,s) 6.74-7.40 (11H,m) 7.54(1H,s) | *3000,1585,1485, 1445,1240,1080 |
| 4 | H | n-C$_3$H$_7$ | H | —SCH$_2$C$_6$H$_5$ | B | Oily matter | 0.78(3H,t) 1.48(2H,m) 3.75(2H,t) 3.86(2H,s) 6.30(1H,s) 6.70-7.60 (12H,m) | 2950,1600,1485, 1450,1240 |
| 5 | H | CH$_3$ | H | —SCH$_2$C$_6$H$_5$ | A | Colorless crystal (75.0-76.5) | 3.60(3H,s) 3.92(2H,s) 6.78(1H,s) 6.80-7.40(11H,m) 7.52(1H,s) | *1595,1495,1255 1075,1020 |
| 6 | H | C$_2$H$_5$ | H | —SCH$_2$C$_6$H$_5$ | A | Colorless crystal (88.5-90.0) | 1.16(3H,t) 3.78(2H,q) 3.94(2H,s) 6.70(1H,s) 6.74-7.40(11H,m) 7.54(1H,s) | *2950,1595,1495, 1245,1070 |
| 7 | H | C$_2$H$_5$ | H | —SCH$_2$C$_6$H$_5$ | — | Oily matter | 1.10,1.16(3H,t) 3.75,3.78(2H,q) 3.86,3.94(2H,s) 6.30,6.70(1H,s) 6.70-7.60(12H,m) | 1600,1485,1450 1240 |
| 8 | H | n-C$_4$H$_9$ | H | —SCH$_2$C$_6$H$_5$ | A | Colorless crystal (60.5-61.5) | 0.70-1.80(7H,br) 3.78(2H,t) 3.94(2H,s) 6.70(1H,s) 6.74-7.40 (11H,m) 7.54(1H,s) | *2950,1585,1485, 1440,1240,1080 |
| 9 | H | n-C$_4$H$_9$ | H | —SCH$_2$C$_6$H$_5$ | — | Oily matter | 0.70-1.80(7H,br) 3.60-3.90(4H,m) 6.30,6.70(1H,s) 6.74-7.50(12H,m) | 2950,1600,1485, 1450,1240 |
| 10 | H | n-C$_5$H$_{11}$ | H | —SCH$_2$C$_6$H$_5$ | — | Oily matter | 0.70-1.80(9H,br) 3.60-3.90(4H,m) 6.30,6.70(1H,s) 6.74-7.50(12H,m) | 2950,1600,1485, 1450,1240 |
| 11 | H | n-C$_6$H$_{13}$ | H | —SCH$_2$C$_6$H$_5$ | — | Oily matter | 0.70-1.80(11H,br) 3.60-3.90(4H,m) 6.30,6.70(1H,s) 6.74-7.50(12H,m) | 2950,1600,1485, 1450,1240 |
| 12 | H | n-C$_7$H$_{15}$ | H | —SCH$_2$C$_6$H$_5$ | — | Oily matter | 0.70-1.80(13H,br) 3.60-3.90(4H,m) 6.30,6.70(1H,s) 6.74-7.50(12H,m) | 2950,1600,1485, 1450,1245 |
| 13 | H | n-C$_8$H$_{17}$ | H | —SCH$_2$C$_6$H$_5$ | — | Oily matter | 0.70-1.80(15H,br) 3.60-3.90(4H,m) 6.30,6.70(1H,s) 6.74-7.50(12H,m) | 2950,1600,1485, 1450,1245 |
| 14 | H | n-C$_9$H$_{19}$ | H | —SCH$_2$C$_6$H$_5$ | — | Oily matter | 0.70-1.80(17H,br) 3.60-3.90(4H,m) 6.30,6.70(1H,s) 6.74-7.50(12H,m) | 2950,1600,1485, 1450,1245 |
| 15 | H | —CH(CH$_3$)$_2$ | H | —SCH$_2$C$_6$H$_5$ | — | Oily matter | 1.05(6H,d) 3.86,3.94(1H,s) 4.46(1H,m) 6.30,6.70(1H,s) 6.74-7.60(12H,m) | 3000,1600,1485, 1450,1375,1245 |
| 16 | H | —CH$_2$—CH=CH$_2$ | H | —SCH$_2$C$_6$H$_5$ | — | Oily matter | 3.86,3.94(1H,s) 4.38(2H,d) 4.96-6.00(3H,m) 6.30,6.70(1H,s) 6.74-7.60(12H,m) | 3050,1600,1490, 1450,1420,1230 |
| 17 | H | n-C$_3$H$_7$ | H | —SCH$_2$C$_6$H$_5$ | A | Colorless crystal (HCl) (167.0-168.5) | 0.86(3H,t) 1.47(2H,m) 3.76(2H,t) 4.04(2H,s) 6.75(1H,s) 6.76-7.60 (1H,m) 8.22(1H,s) | *3000,1600,1450, 1250,1240,980 |

Note 1: In the column under "IR", asterisk "*" indicates measurement with KBr.
Note 2: In the column under "Isomer type", "A" means compounds derived from Compound 1 or compounds derived from Compound 2 or compounds having the same steric configuration as the compounds derived from Compound 2, and "—" indicates a mixture of isomers A and B. The same definition applies to subsequent tables.

EXAMPLE 5

To a suspension of 1.02 g of imidazole, 1.52 g of triethylamine and 30 ml of dry methylene chloride, 1.78 g of thionyl chloride was added with ice-cooling. The resulting mixture was stirred for 30 minutes, followed by addition of 2.42 g of 2-n-propylthio-2'-hydroxyacetophenone and a solution consisting of 1.16 g of triethylamine and 5 ml of dry methylene chloride. The reaction mixture was stirred at room temperature for further 2 hours. Ice water was then added to the reaction mixture, followed by its extraction with methylene chloride. The organic, i.e., methylene chloride layer was washed with water, dried over magnesium sulfate, and then concentrated. The residue was dissolved in chloroform. The chloroform solution was subjected to chromatography on a silica gel column. Upon concentration of the resulting eluate, 0.2 g of Isomer A (Compound 19; m.p. 191°-192° C.) and 1.1 g of Isomer B (Compund 18; m.p. 127°-128° C.) of 1-(2-hydroxyphenyl)-1-imidazolyl-2-n-propylthioethylene were obtained respectively as colorless crystals.

EXAMPLE 6

To a suspension of 4.08 g of imidazole and 30 ml of dry methylene chloride, 1.78 g of thionyl chloride was added with ice-cooling. The resultant mixture was stirred for 30 minutes, followed by an addition of 2.10 g of 2-n-propylthio-2'-hydroxyacetophenone. The thus-obtained mixture was stirred at room temperature for 2 hours. Ice water was then added to the reaction mixture, followed by its extraction with methylene chloride. The methylene chloride extract was then subjected to a post treatment in the same manner as in Example 5. The reaction product was separated by column chromatography, thereby obtaining 0.2 g of Isomer A (Compound 18) and 1.0 g of Isomer B (Compound 19) of 1-(2-hydroxyphenyl)-1-imidazolyl-2-n-propylthioethylene as colorless crystals respectively.

EXAMPLE 7

Dissolved in 2 ml of dry dimethylformamide was 100 mg of Compound 18 obtained in Example 5, to which 15 mg of sodium hydroxide was added. After stirring the resultant mixture at room temperature for 30 minutes, 55 mg of n-butyl bromide was added and the resulting mixture was left over at room temperature for 4 hours. Water was then added to the reaction mixture, followed by its extraction with ethyl ether. The ethyl ether extract was dried over magnesium sulfate and the ethyl ether was then distilled off. The residue was purified by chromatography on a silica gel column. From a chloroform eluate, 100 mg of Isomer A (Compound 20) of 1-(2-n-butyloxyphenyl)-1-imidazolyl-2-n-propylthioethylene was obtained as colorless crystals.

EXAMPLE 8

After adding an equivalent amount of hydrogen chloride to 200 mg of an oily substance which was Isomer B of 1-(2-n-butyloxyphenyl)-1-imidazolyl-2-n-propylthioethylene obtained from Compound 19 in the same manner as in Example 6, the resultant precipitate was recrystallized from ethyl acetate/acetone to obtain 140 mg of Isomer B (Compound 21) of 1-(2-n-butyloxyphenyl)-1-imidazolyl-2-n-propylthioethylene hydrochloride as colorless crystals.

EXAMPLE 9

Compounds 22-60 shown in Table 2-B were each prepared in the same manner as in any one of Examples 5-8. Physical properties of Compounds 18-21 are also given in the table.

TABLE 2-B

| Comp. No. | Structure Formula (I) | | | | Isomer type | Characteristics | | |
|---|---|---|---|---|---|---|---|---|
| | $R_1$ | $R_2$ | $R_3$ | $R_4$ | | Appearance (m.p. °C.) | NMR δ ppm in $CDCl_3$ | $IR\nu_{max}^{NaCl}cm^{-1}$ |
| 18 | H | H | H | $-S-n-C_3H_7$ | A | Colorless crystal (191–192) | 1.01(3H,t) 1.72(2H,m) 2.77(2H,t) 6.70(1H,s) 6.80–7.40(6H,m) 7.69(1H,s) | *2970,1590,1495, 1445,1090 |
| 19 | H | H | H | $-S-n-C_3H_7$ | B | Colorless crystal (127–128) | 0.98(3H,t) 1.66(2H,m) 2.68(2H,t) 6.40(1H,s) 6.80–7.40(6H,m) 7.46(1H,s) | *2970,1595,1495, 1455,1230,1080 |
| 20 | H | $n-C_4H_9$ | H | $-S-n-C_3H_7$ | A | Colorless crystal (77–78) | 0.80–1.90(12H,m) 2.72(2H,t) 3.88 (2H,t) 6.84(1H,s) 6.80–7.30 (6H,m) 7.68(1H,s) | *2940,1585,1495, 1245 |
| 21 | H | $n-C_4H_9$ | H | $-S-n-C_3H_7$ | B | Colorless crystal (HCl) (109.5–111) | 0.70–1.90(12H,m) 2.84(2H,t) 3.82(2H,t) 6.80–7.60(7H,m) 8.75(1H,s) | *2940,1650,1560, 1455,1240 |
| 22 | H | $CH_3$ | H | $-SCH_3$ | B | Oily matter | 2.28(3H,s) 3.68(3H,s) 6.38(1H,s) 6.70–7.50(7H,m) | 2930,1600,1490, 1250,1025 |
| 23 | H | $C_2H_5$ | H | $-SCH_3$ | B | Colorless crystal (96–97) | 1.14(3H,t) 2.28(3H,s) 3.88(2H,q) 6.36(1H,s) 6.70–7.50(7H,m) | *3000,1595,1485, 1255,1050 |
| 24 | H | $n-C_3H_7$ | H | $-SCH_3$ | B | Colorless crystal (67–68) | 0.82(3H,t) 1.52(2H,m) 2.28(3H,s) 3.78(2H,t) 6.36(1H,s) 6.70–7.50(7H,m) | *2950,1595,1485, 1255,1045 |
| 25 | H | $n-C_4H_9$ | H | $-SCH_3$ | B | Colorless crystal (63.5–64.5) | 0.86(3H,t) 1.00–1.70(4H,m) 2.28 (3H,s) 3.83(2H,t) 6.36(1H,s) 6.70–7.50(7H,m) | *2950,1595,1485, 1255 |
| 26 | H | $n-C_5H_{11}$ | H | $-SCH_3$ | B | Colorless crystal (38.5–39.5) | 0.86(3H,t) 1.01–1.70(6H,m) 2.28 (3H,s) 3.80(2H,t) 6.34(1H,s) 6.70–7.50(7H,m) | *2950,1595,1485, 1255,1070 |
| 27 | H | $n-C_6H_{13}$ | H | $-SCH_3$ | B | Colorless crystal (65.5–66.5) | 0.70–1.70(11H,m) 2.28(3H,s) 3.80(2H,t) 6.34(1H,s) 6.70–7.50(7H,m) | *2940,1600,1485, 1235,1115 |
| 28 | H | $n-C_7H_{15}$ | H | $-SCH_3$ | B | Colorless crystal (67.5–68.5) | 0.70–1.70(13H,m) 2.28(3H,s) 3.80(2H,t) 6.34(1H,s) 6.70–7.50(7H,m) | *2930,1595,1485, 1230,1150 |
| 29 | H | $n-C_8H_{17}$ | H | $-SCH_3$ | B | Colorless crystal (37–38) | 0.70–1.70(15H,m) 2.28(3H,s) 3.80(2H,t) 6.34(1H,s) 6.70–7.50 (7H,m) | *2930,1595,1480, 1240,1110 |
| 30 | H | $CH_3$ | H | $-SC_2H_5$ | B | Oily | 1.31(3H,t) 2.72(2H,q) 3.68(3H,s) | 2970,1600,1490, |

TABLE 2-B-continued

| Comp. No. | R₁ | R₂ | R₃ | R₄ | Isomer type | Appearance (m.p. °C.) | NMR δ ppm in CDCl₃ | IR $\nu_{max}^{NaCl}$ cm⁻¹ |
|---|---|---|---|---|---|---|---|---|
| 31 | H | C₂H₅ | H | —SC₂H₅ | B | matter Colorless crystal (79–80) | 6.43(1H,s) 6.70–7.50(7H,m) 1.14(3H,t) 1.31(3H,t) 2.72(2H,q) 3.88(2H,q) 6.40(1H,s) 6.70–7.50 (7H,m) | 1250,1030 *2980,1595,1485, 1450,1245,1040 |
| 32 | H | n-C₃H₇ | H | —SC₂H₅ | B | Colorless crystal (48–49) | 0.83(3H,t) 1.32(3H,t) 1.20–1.70 (2H,m) 2.72(2H,q) 3.78(2H,t) 6.40(1H,s) 6.70–7.50(7H,m) | *2950,1600,1490, 1455,1250 |
| 33 | H | n-C₄H₉ | H | —SC₂H₅ | B | Colorless crystal (33.5–34.5) | 0.86(3H,t) 1.00–1.70(4H,m) 1.30 (3H,t) 2.71(2H,q) 3.82(2H,t) 6.39(1H,s) 6.70–7.50(7H,m) | *2950,1595,1480, 1240,1105 |
| 34 | H | n-C₅H₁₁ | H | —SC₂H₅ | B | Colorless crystal (51–52) | 0.70–1.70(12H,m) 2.70(2H,q) 3.80 (2H,t) 6.39(1H,s) 6.70–7.50 (7H,m) | *2950,1595,1480, 1240,1230,1105 |
| 35 | H | n-C₆H₁₃ | H | —SC₂H₅ | B | Colorless crystal (51.5–53) | 0.70–1.70(14H,m) 2.71(2H,q) 3.80 (2H,t) 6.39(1H,s) 6.70–7.50 (7H,m) | *2930,1595,1485, 1245,1230,1110 |
| 36 | H | n-C₇H₁₅ | H | —SC₂H₅ | B | Colorless crystal (56–57) | 0.70–1.70(16H,m) 2.70(2H,q) 3.80 (2H,t) 6.40(1H,s) 6.70–7.50 (7H,m) | *2930,1595,1490, 1450,1250,1110 |
| 37 | H | CH₃ | H | —S—n-C₃H₇ | B | Colorless crystal (71–72) | 0.96(3H,t) 1.64(2H,m) 2.64(2H,t) 3.66(3H,s) 4.38(1H,s) 6.70–7.50 (7H,m) | *2970,1600,1490, 1250,1055 |
| 38 | H | C₂H₅ | H | —S—n-C₃H₇ | B | Colorless crystal (68–69) | 0.99(3H,t) 1.14(3H,t) 1.66(2H,m) 2.68(2H,t) 3.88(2H,q) 6.38(1H,s) 6.70–7.50(7H,m) | *2960,1595,1485, 1245,1040 |
| 39 | H | n-C₃H₇ | H | —S—n-C₃H₇ | B | Oily matter | 0.70–1.90(10H,m) 2.68(2H,t) 3.78 (2H,t) 6.40(1H,s) 6.70–7.50 (7H,m) | 2960,1595,1485, 1245,980 |
| 40 | H | n-C₅H₁₁ | H | —S—n-C₃H₇ | B | Colorless crystal (HCl) (112.5–124) | 0.70–1.90(14H,m) 2.84(2H,t) 3.82 (2H,t) 6.80–7.60(7H,m) 8.75(1H,s) | *2950,1600,1565, 1445,1255 |
| 41 | H | n-C₆H₁₃ | H | —S—n-C₃H₇ | — | Oily matter | 0.70–1.90(16H,m) 2.68(2H,t) 3.78 (2H,t) 6.40,6.80(1H,s) 6.80–7.60 (7H,m) | 2970,2940,1600, 1485,1245,1110 |
| 42 | H | n-C₇H₁₅ | H | —S—n-C₃H₇ | — | Oily matter | 0.70–1.90(18H,m) 2.68(2H,t) 3.78 (2H,t) 6.40,6.80(1H,s) 6.80–7.60 (7H,m) | 2940,1600,1485, 1245 |
| 43 | H | n-C₈H₁₇ | H | —S—n-C₃H₇ | — | Oily matter | 0.70–1.90(20H,m) 2.68(2H,t) 3.78 (2H,t) 6.40,6.80(1H,s) 6.80–7.60 (7H,m) | 2940,1595,1485, 1450,1245,1050 |
| 44 | H | CH₃ | H | —S—n-C₄H₉ | B | Colorless crystal (72–73.5) | 0.90(3H,t) 1.10–1.80(4H,m) 2.68 (2H,t) 3.68(3H,s) 6.41(1H,s) 6.70–7.50(7H,m) | *2950,1595,1490, 1245,1070 |
| 45 | H | C₂H₅ | H | —S—n-C₄H₉ | B | Oily matter | 0.70–1.80(10H,m) 2.68(2H,t) 3.86 (2H,q) 6.39(1H,s) 6.70–7.60 (7H,m) | 2970,2940,1600, 1495,1450,1250, 1120 |
| 46 | H | n-C₃H₇ | H | —S—n-C₄H₉ | B | Oily matter | 0.70–1.80(12H,m) 2.68(2H,t) 3.80 (2H,t) 6.37(1H,s) 6.70–7.50 (7H,m) | 2970,1595,1490, 1450,980 |
| 47 | H | n-C₄H₉ | H | —S—n-C₄H₉ | B | Oily matter | 0.70–1.80(14H,m) 2.68(2H,t) 3.80 (2H,t) 6.37(1H,s) 6.70–7.50 (7H,m) | 2960,1595,1485, 1450,1245,1110 |
| 48 | H | n-C₅H₁₁ | H | —S—n-C₄H₉ | B | Oily matter | 0.70–1.80(16H,m) 2.68(2H,t) 3.80 (2H,t) 6.37(1H,s) 6.70–7.50 (7H,m) | 2960,1595,1490, 1450,1250,1110 |
| 49 | H | C₂H₅ | H | —S—n-C₅H₁₁ | B | Oily matter | 0.70–1.80(12H,m) 2.68(2H,t) 3.86 (2H,q) 6.38(1H,s) 6.80–7.60 (7H,m) | 2940,1595,1485, 1450,1245 |
| 50 | H | —CH₂—CH=CH₂ | H | —S—n-C₆H₁₃ | B | Oily matter | 0.70–1.80(11H,m) 2.68(2H,t) 4.32 (2H,m) 5.02(2H,m) 5.60(1H,m) 6.38(1H,s) 6.80–7.60(7H,m) | 2940,1595,1485, 1450,1245,1045 |
| 51 | H | —CH₂CF₃ | H | —S—n-C₃H₇ | B | Oily matter | 0.98(3H,t) 1.66(2H,m) 2.68(2H,t) 4.20(2H,q) 6.45(1H,s) 6.80–7.60(7H,m) | 2980,1600,1490, 1240,1165 |
| 52 | H | —CH₂CF₃ | H | —S—n-C₄H₉ | B | Oily matter | 0.90(3H,t) 1.10–1.80(4H,m) 2.68 (2H,t) 4.20(2H,q) 6.44(1H,s) 6.80–7.60(7H,m) | 2970,1600,1490, 1240,1165 |
| 53 | H | —CH₂C₆H₅ | H | —SCH₃ | B | Colorless crystal (85.5–86.5) | 2.27(3H,s) 4.94(2H,s) 6.36(1H,s) 6.80–7.50(12H,m) | *3130,2940,1595, 1485,1240,1220 1110 |
| 54 | H | 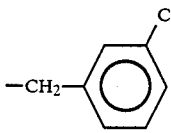 —CH₂—⌬—Cl | H | —SCH₃ | B | Oily matter | 2.27(3H,s) 4.95(2H,s) 6.36(1H,s) 6.80–7.50(11H,m) | 3130,2940,1500, 1490,1245,1120 |

TABLE 2-B-continued

| Comp. No. | Structure Formula (I) | | | | Isomer type | Appearance (m.p. °C.) | NMR δ ppm in CDCl$_3$ | IR$\nu_{max}^{NaCl}$cm$^{-1}$ |
|---|---|---|---|---|---|---|---|---|
| | $R_1$ | $R_2$ | $R_3$ | $R_4$ | | | | |
| 55 | H | n-C$_3$H$_7$ | H | —SCH$_2$CH=CH$_2$ | B | Oily matter | 0.80(3H,t) 1.52(2H,m) 3.28(2H,d) 3.76(2H,t) 5.00–5.32(2H,m) 5.60–6.06(1H,m) 6.32(1H,s) 6.70–7.60(7H,m) | 2970,1600,1490, 1455,1245,1120 |
| 56 | H | C$_2$H$_5$ | H | —SC(CH$_3$)$_3$ | B | Oily matter | 1.12(3H,t) 1.36(9H,s) 3.85(2H,q) 6.55(1H,s) 6.70–7.60(7H,m) | 2970,1600,1485, 1450,1250,1050 |
| 57 | H | n-C$_3$H$_7$ | H | —SC(CH$_3$)$_3$ | B | Oily matter | 0.80(3H,t) 1.36(9H,s) 1.54(2H,m) 3.76(2H,t) 6.55(1H,s) 6.70–7.60 (7H,m) | 2970,1600,1490, 1455,1250,1160 |
| 58 | H | n-C$_3$H$_7$ | H | —SCH$_3$ | A | Oily matter | 0.94(3H,t) 1.66(2H,m) 2.32(3H,s) 3.84(2H,t) 6.72(1H,s) 6.76–7.40 (6H,m) 7.56(1H,s) | 2940,1595,1490, 1250,1070 |
| 59 | H | n-C$_4$H$_9$ | H | —SCH$_3$ | A | Oily matter | 0.92(3H,t) 1.10–1.80(4H,m) 2.32 (3H,s) 3.88(2H,t) 6.74(1H,s) 6.76–7.40(6H,m) 7.56(1H,s) | 2940,1595,1490, 1250,1070 |
| 60 | H | n-C$_5$H$_{11}$ | H | —SCH$_3$ | A | Oily matter | 0.90(3H,t) 1.10–1.80(6H,m) 2.32 (3H,s) 3.86(2H,t) 6.74(1H,s) 6.76–7.40(6H,m) 7.54(1H,s) | 2940,1595,1490, 1250,1070 |

EXAMPLE 10

To a suspension of 1.02 g of imidazole, 1.52 g of triethylamine and 30 ml of dry methylene chloride, 1.78 g of thionyl chloride was added with ice-cooling. The resultant mixture was stirred for 30 minutes, followed by addition of 2.44 g of 2-phenylthio-2'-hydroxyacetophenone and a solution consisting of 1.16 g of triethylamine and 5 ml of dry methylene chloride. The reaction mixture was stirred at room temperature for further 2 hours. Ice water was then added to the reaction mixture, followed by its extraction with methylene chloride. The organic, i.e., methylene chloride layer was washed with water, dried over magnesium sulfate, and then concentrated. The residue was dissolved in chloroform. The chloroform solution was subjected to chromatography on a silica gel column. Upon concentration of the resulting eluate, 0.2 g of Isomer A (Compound 61; m.p. 235.5°–237° C.) and 0.9 g of Isomer B (Compound 62; m.p. 152.5°–154° C.) of 1-(2-hydroxyphenyl)-1-imidazolyl-2-phenylthioethylene were obtained respectively as colorless crystals.

EXAMPLE 11

To a suspension of 4.08 g of imidazole and 30 ml of dry methylene chloride, 1.78 g of thionyl chloride was added with ice-cooling. The resultant mixture was stirred for 30 minutes, followed by an addition of 2.10 g of 2-phenylthio-2'-hydroxyacetophenone. The thus-obtained mixture was stirred at room temperature for 2 hours. Ice water was then added to the reaction mixture, followed by its extraction with methylene chloride. The methylene chloride extract was then subjected to a post treatment in the same manner as in Example 10. The reaction product was separated by column chromatography, thereby obtaining 0.2 g of Isomer A (Compound 61) and 1.0 g of Isomer B (Compound 62) of 1-(2-hydroxyphenyl)-1-imidazolyl-2-phenylthioethylene as colorless crystals respectively.

EXAMPLE 12

Dissolved in 2 ml of dry dimethylformamide was 100 mg of Compound 61 obtained in Example 10, to which 15 mg of sodium hydroxide was added. After stirring the resultant mixture at room temperature for 30 minutes, 45 mg of ethyl bromide was added and the resulting mixture was left over at room temperature for 4 hours. Water was then added to the reaction mixture, followed by its extraction with ethyl ether. The ethyl ether extract was dried over magnesium sulfate and the ethyl ether was then distilled off. The residue was purified by chromatography on a silica gel. From a chloroform eluate, 100 mg of Isomer A (Compound 63) of 1-(2-ethyloxyphenyl)-1-imidazolyl-2-phenylthioethylene was obtained as colorless crystals.

EXAMPLE 13

After adding an equivalent amount of hydrogen chloride to 100 mg of an oily substance which was Isomer B (Compound 66) of 1-(2-n-butyloxyphenyl)-1-imidazolyl-2-phenylthioethylene obtained from Compound 62 in the same manner as in Example 10, the resultant precipitate was recrystallized from ethyl acetate/acetone to obtain 75 mg of Isomer B (Compound 95) of 1-(2-n-butyloxyphenyl)-1-imidazolyl-2-phenylthioethylene hydrochloride as colorless crystals.

EXAMPLE 14

Compounds 64, 65 and 67–94 shown in Table 2-C were each prepared in the same manner as in any one of Examples 10–13. Physical properties of Compounds 61–63, 66 and 95 are also given in the table.

TABLE 2-C

| Comp. No. | Structure Formula (I) | | | | Isomer type | Appearance (m.p. °C.) | NMR δ ppm in CDCl$_3$ | IR$\nu_{max}^{NaCl}$cm$^{-1}$ |
|---|---|---|---|---|---|---|---|---|
| | $R_1$ | $R_2$ | $R_3$ | $R_4$ | | | | |
| 61 | H | H | H | —SC$_6$H$_5$ | A | Colorless crystal (235.5–237) | 6.85(1H,s) 7.00–7.50(12H,m) | *3130,1590,1440, 1245,1080 |
| 62 | H | H | H | —SC$_6$H$_5$ | B | Colorless crystal (152.5–154) | 6.65(1H,s) 6.70–7.45(11H,m) 7.50(1H,s) | *3130,1595,1450, 1230,1090 |

TABLE 2-C-continued

| Comp. No. | R₁ | R₂ | R₃ | R₄ | Isomer type | Appearance (m.p. °C.) | NMR δ ppm in CDCl₃ | IR $\nu_{max}^{NaCl}$ cm$^{-1}$ |
|---|---|---|---|---|---|---|---|---|
| 63 | H | C₂H₅ | H | —SC₆H₅ | A | Colorless crystal (96–97) | 1.25(3H,t) 3.87(2H,q) 6.70–7.50 (12H,m) 7.70(1H,s) | *3070,1585,1480, 1235,1080 |
| 64 | H | n-C₃H₇ | H | —SC₆H₅ | B | Oily matter | 0.83(3H,t) 1.54(2H,m) 3.80(2H,t) 6.62(1H,s) 6.70–7.50(12H,m) | 2970,1595,1480, 1240,1070 |
| 65 | H | n-C₃H₇ | H | —SC₆H₅ | A | Colorless crystal (75–76) | 0.88(3H,t) 1.65(2H,m) 3.87(2H,t) 6.70–7.50(12H,m) 7.70(1H,s) | *2970,1585,1480, 1230,1065 |
| 66 | H | n-C₄H₉ | H | —SC₆H₅ | B | Oily matter | 0.70–1.80(7H,m) 3.80(2H,t) 6.45(1H,s) 6.70–7.50(12H,m) | 2960,1595,1580, 1480,1220,1015 |
| 67 | H | n-C₄H₉ | H | —SC₆H₅ | A | Colorless crystal (97–98) | 0.70–1.80(7H,m) 3.88(2H,t) 6.73–7.50(12H,m) 7.70(1H,s) | *2960,1590,1440, 1240,1060 |
| 68 | H | —CH₂CH=CH₂ | H | —SC₆H₅ | B | Oily matter | 4.32(2H,m) 5.02(2H,m) 5.60 (1H,m) 6.45(1H,s) 6.70–7.50 (12H,m) | 3080,1595,1580, 1480,1240 |
| 69 | H | C₂H₅ | H | —OC₆H₅ | B | Oily matter | 1.20(3H,t) 3.86(2H,q) 6.70–7.50 (12H,m) 7.48(1H,s) | 3070,3000,1670, 1600,1490,1230 |
| 70 | H | n-C₃H₇ | H | —OC₆H₅ | B | Oily matter | 0.88(3H,t) 1.62(2H,m) 3.78(2H,t) 6,70–7.50(12H,m) 7.48(1H,s) | 3070,2970,1670, 1600,1490,1230 |
| 71 | H | n-C₄H₉ | H | —OC₆H₅ | B | Oily matter | 0.88(3H,t) 1.00–1.70(4H,m) 3.80 (2H,t) 6.70–7.50(12H,m) 7.50 (1H,s) | 3070,2970,1670, 1600,1490,1230 |
| 72 | H | n-C₅H₁₁ | H | —OC₆H₅ | B | Oily matter | 0.86(3H,t) 1.00–1.70(6H,m) 3.80 (2H,t) 6.70–7.50(12H,m) 7.50 (1H,s) | 3070,2970,1670, 1600,1490,1230 |
| 73 | H | n-C₆H₁₃ | H | —OCH₃ | B | Oily matter | 0.88(3H,t) 1.00–1.70(8H,m) 3.74 (3H,s) 3.84(2H,t) 6.48(1H,s) 6.70–7.50(6H,m) 7.56(1H,s) | 2950,1680,1600, 1495,1450,1240 |
| 74 | H | n-C₃H₇ | H | —OCH₃ | B | Oily matter | 0.88(3H,t) 1.60(2H,m) 3.72(3H,s) 3.80(2H,t) 6.48(1H,s) 6.70–7.50(6H,m) 7.56(1H,s) | 2950,1680,1600, 1495,1450,1240 |
| 75 | H | n-C₄H₉ | H | —OCH₃ | B | Oily matter | 0.90(3H,t) 1.00–1.70(4H,m) 3.74 (3H,s) 3.84(2H,t) 6.50(1H,s) 6.70–7.50(6H,m) 7.56(1H,s) | 2950,1680,1600, 1495,1450,1240 |
| 76 | H | n-C₅H₁₁ | H | —OCH₃ | B | Oily matter | 0.88(3H,t) 1.00–1.70(6H,m) 3.74 (3H,s) 3.84(2H,t) 6.50(1H,s) 6.70–7.50(6H,m) 7.56(1H,s) | 2950,1680,1600, 1495,1450,1240 |
| 77 | H | n-C₄H₉ | H | Br | B | Oily matter | 0.86(3H,t) 1.00–1.70(4H,m) 3.78 (2H,t) 6.48(1H,s) 6.70–7.50 (7H,m) | 2970,1600,1490, 1450,1110 |
| 78 | H | n-C₆H₁₃ | H | Br | B | Oily matter | 0.86(3H,t) 1.00–1.70(8H,m) 3.78 (2H,t) 6.47(1H,s) 6.70–7.50 (7H,m) | 2950,1600,1490, 1450,1250,1050 |
| 79 | H | n-C₈H₁₇ | H | Br | B | Oily matter | 0.88(3H,t) 1.00–1.70(12H,m) 3.78 (2H,t) 6.48(1H,s) 6.70–7.50 (7H,m) | 2950,1600,1490, 1450,1250,1030 |
| 80 | H | C₂H₅ | H | Cl | B | Colorless crystal (94–95) | 1.18(3H,t) 3.88(2H,q) 6.50(1H,s) 6.70–7.50(6H,m) 7.64(1H,s) | *3070,1630,1600, 1485,1255,1070 |
| 81 | H | n-C₄H₉ | H | Cl | B | Oily matter | 0.90(3H,t) 1.00–1.70(4H,m) 3.82 (2H,t) 6.48(1H,s) 6.70–7.50 (6H,m) 7.64(1H,s) | 2970,1600,1485, 1250,1070 |
| 82 | H | n-C₅H₁₁ | H | Cl | B | Oily matter | 0.90(3H,t) 1.00–1.70(6H,m) 3.82 (2H,t) 6.49(1H,s) 6.70–7.50 (6H,m) 7.64(1H,s) | 2950,1600,1485, 1250,1070 |
| 83 | H | n-C₆H₁₃ | H | Cl | B | Oily matter | 0.88(3H,t) 1.00–1.70(8H,m) 3.82 (2H,t) 6.49(1H,s) 6.70–7.50 (6H,m) 7.64(1H,s) | 2950,1600,1485, 1250,1070 |
| 84 | H | n-C₃H₇ | H | F | B | Oily matter | 0.84(3H,t) 1.56(2H,m) 3.82(2H,t) 6.92((1H,d) 6.70–7.50(6H,m) 7.56(1H,s) | 2970,1680,1600, 1490,1450,1250 |
| 85 | H | n-C₄H₉ | H | F | B | Oily matter | 0.88(3H,t) 1.00–1.70(4H,m) 3.84 (2H,t) 6.90(1H,d) 6.70–7.50 (6H,m) 7.56(1H,s) | 2940,1680,1600, 1490,1450,1250 |
| 86 | H | n-C₅H₁₁ | H | F | B | Oily matter | 0.88(3H,t) 1.00–1.70(6H,m) 3.84 (2H,t) 6.90(1H,d) 6.70–7.50 (6H,m) 7.56(1H,s) | 2940,1680,1600, 1490,1450,1250 |
| 87 | H | n-C₆H₁₃ | H | F | B | Oily matter | 0.88(3H,t) 1.00–1.70(8H,m) 3.84 (2H,t) 6.90(1H,d) 6.70–7.50 (6H,m) 7.56(1H,s) | 2940,1680,1600, 1490,1450,1250 |
| 88 | 5-Cl | n-C₅H₁₁ | H | —SCH₃ | — | Oily matter | 0.88(3H,t) 1.00–1.70(6H,m) 2.32, 2.35(3H,s) 3.78(2H,t) 6.36(1H,s) 6.70–7.50(5H,m) 7.45,7.50(1H,s) | 2940,1595,1490, 1250,1080 |
| 89 | 5-CH | n-C₄H₉ | H | —SCH₃ | B | Oily matter | 0.88(3H,t) 1.00–1.70(4H,m) 2.30 (6H,s) 3.78(2H,t) 6.36(1H,s) 6.70–7.50(5H,m) 7.45(1H,s) | 2970,1610,1490, 1250,1080 |

TABLE 2-C-continued

| Comp. No. | R₁ | R₂ | R₃ | R₄ | Isomer type | Appearance (m.p. °C.) | NMR δ ppm in CDCl₃ | IR $\nu_{max}^{NaCl}$ cm$^{-1}$ |
|---|---|---|---|---|---|---|---|---|
| 90 | H | n-C₃H₇ | H | —SCH₂—(2-Cl-C₆H₄) | B | Colorless crystal (96–97) | 0.80(3H,t) 1.50(2H,m) 3.76(2H,t) 3.80(2H,s) 6.28(1H,s) 6.70–7.50 (11H,m) | *2970,1600,1490, 1245,1050 |
| 91 | H | n-C₃H₇ | H | —SCH₂—(4-Cl-C₆H₄) | — | Oily matter | 0.78,0.86(3H,t) 1.20–1.70(2H,m) 3.60–3.90(4H,m) 6.26,6.62(1H,s) 6.70–7.50(11H,m) | 2970,1600,1490, 1250 |
| 92 | H | n-C₄H₉ | H | —SCH₂-furyl | — | Oily matter | 0.70–1.70(7H,m) 3.70–4.00(4H,m) 6.30(2H,m) 6.42,6.85(1H,s) 6.80–7.60(8H,m) | 3120,2970,1600, 1490,1450,1250 |
| 93 | H | n-C₄H₉ | Br | Br | No isomer | Colorless crystal (69–70) | 0.95(3H,t) 1.10–1.80(4H,m) 3.83 (2H,t) 6.60–7.40(6H,m) 7.50 (1H,s) | *2970,1600,1485, 1450,1280,1260, 1050 |
| 94 | H | n-C₆H₁₃ | Br | Br | No isomer | Oily matter | 0.70–1.90(11H,m) 3.83(2H,t) 6.60–7.40(6H,m) 7.50(1H,s) | 2950,1600,1485, 1450,1250,1050 |
| 95 | H | n-C₄H₉ | H | —SC₆H₅ | B | Colorless crystal (HCl) (143–145) | 0.88(3H,t) 1.00–1.70(4H,m) 3.86 (2H,t) 6.80–7.60(12H,m) 8.34 (1H,s) | *3000,1595,1490, 1450,1240,1070 |

Having now fully described the invention, it will be apparent to one of ordinary skill in the art that many changes and modifications can be made thereto without departing from the spirit or scope of the invention as set forth herein.

What is claimed as new and is secured by Letters Patent is:

1. An imidazole derivative represented by formula (I):

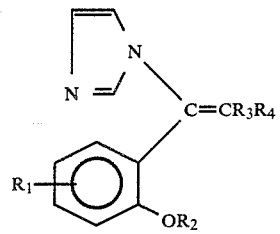

wherein R₁ is a hydrogen, halogen atom or a lower alkyl group; R₂ is a hydrogen atom, a C₁–C₉ alkyl, lower alkenyl, lower haloalkyl, benzyl group, chlorobenzyl group; R₃ is a hydrogen or halogen atom; and R₄ is a benzylthio group, a chlorobenzylthio group, a phenylthio group, a C₁–C₆ alkylthio group, a lower alkenylthio group, a furfurylthio group, a lower alkoxy group, a phenoxy group or a halogen atom; or an acid addition salt thereof.

* * * * *